Figure 1:
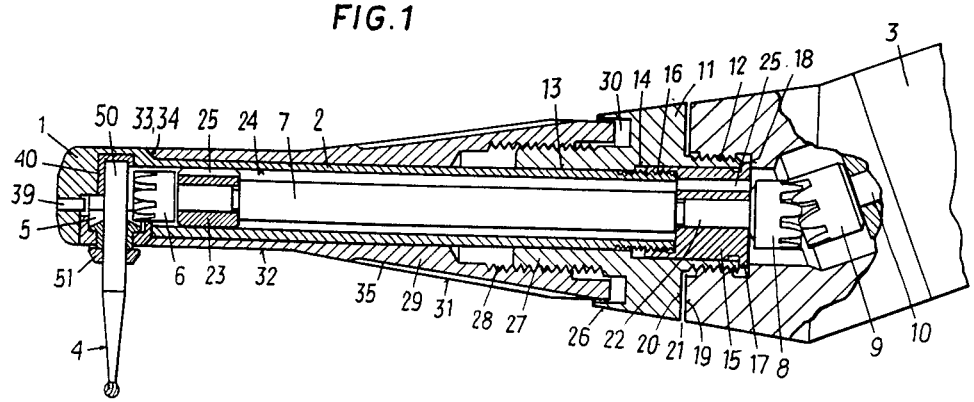

United States Patent [19]

Rosenstatter

[11] Patent Number: 4,564,354
[45] Date of Patent: Jan. 14, 1986

[54] ANGLE PIECE FOR DENTAL PURPOSES

[75] Inventor: Otto Rosenstatter, Seeham, Austria

[73] Assignee: Dentalwerk Büroos Gesellschaft m.b.H., Bürmoos, Austria

[21] Appl. No.: 616,227
[22] PCT Filed: Sep. 19, 1983
[86] PCT No.: PCT/AT83/00028
 § 371 Date: May 16, 1984
 § 102(e) Date: May 16, 1984
[87] PCT Pub. No.: WO84/01099
 PCT Pub. Date: Mar. 29, 1984

[30] Foreign Application Priority Data

Sep. 21, 1982 [AT] Austria ................. 3509/82

[51] Int. Cl.⁴ .................................. A61C 1/12
[52] U.S. Cl. ....................... 433/133; 433/165
[58] Field of Search ..................... 433/126, 133

[56] References Cited

U.S. PATENT DOCUMENTS 2,010,421 8/1935 Terry ......................... 433/126
2,090,885 8/1937 Clark ......................... 433/126
4,285,671 8/1981 Lustig et al. ................. 433/133

Primary Examiner—Robert Peshock
Attorney, Agent, or Firm—Toren, McGeady, Stanger, Goldberg & Kiel

[57] ABSTRACT

The invention is directed to an angle piece for dental purposes comprising a tool with cylindrical tool shaft (50), which tool is supported in the head part (1) transversely relative to the drive axis or axle and is securely connected with its drive gear wheel (5) and is interchangeable together with the latter and is characterized in that a head bearing (42) on the tool side, which head bearing (42) is insertable in the head part (1) in a form-locking manner, is rotatably and undetachably connected with the tool (4) and in that an outer screw sleeve (29), which is axially displaceable on the head shaft, partly overlaps the head bearing (42) in its inserted position. A construction of the invention provides that the opening of the screw sleeve (29) has a hollow cone (33) which is pressable against a corresponding outer cone face (49) of the head bearing (42).

8 Claims, 5 Drawing Figures

U.S. Patent  Jan. 14, 1986  Sheet 1 of 2  4,564,354

ANGLE PIECE FOR DENTAL PURPOSES

The invention is directed to an angle piece for dental purposes, comprising a tool with cylindrical tool shaft, which tool is supported in the head part transversely relative to the drive axle and is securely connected with its drive gear wheel and is interchangeable together with the latter. In addition, the invention is directed to an apparatus for locking this structural component group, particularly provided that the angle piece is an integral structural component part of the cylindrical head shaft without projecting parts.

In a known angle piece of this type, according to U.S. Pat. No. 4,268,252, a construction of the angle head is described according to which the latter forms the closure of the cylindrical head shaft and does not project over its circular cross-section of the latter. A graduated cross borehole of the head shaft forms the bearing surfaces for the drilling tool formed from the tool shaft and the drive gear wheel fastened on the latter. The end face of the gear wheel on the tool side forms a spherical cap with a radius of curvature equal to the radius of the head shaft and, when the tool is employed, closes so as to be flush with the casing surface of the head shaft. A cylindrical sleeve overlaps the head shaft and the part of the angle head, can either be rotated or axially displaced on the shaft and is provided with openings which, according to the detail shown, either free the cross borehole of the head shaft or partially cover it. as desired, in order to make it possible to introduce or hold the tool, respectively, in the working position. This construction of an angle piece head offers the possibility of a very small manner of construction without projecting parts of the head, but it also involves disadvantages. For example, because of the fact that the bearing of the driven gear wheel connected with the tool shaft is effected in the cross borehole of the angle piece shaft, the diameter of the bearing on the tool side is attached to the largest diameter of the gear wheel in order to be able to remove the drive from the head. This bearing is therefore greatly heated during operation at the high speeds usual today and, moreover, this has the result that the entire head shaft must be replaced during the necessary replacement after wear, which means costly repairs. In addition, it is disadvantageous that the gear wheel member does not have a sufficient flat bearing frontally against the tool, since its spherical end face has line contact against the wall of the locking sleeve at only two places at best and rapid wear will result at this place. A further disadvantage is to be seen in that the longitudinal or transverse slots provided for passing the tool shaft in the locking sleeve interrupts the end bearing surface of the gear wheel drive, wherein the edges of the slot act on the rotating end face of the gear wheel like scrapers and cause the highly undesirable emergence of lubricant in the direction of the tool. Finally, it must be mentioned that in order to change the tool the locking sleeve embracing the head shaft must be turned or axially displced by hand and that it can be very troublesome to handle this thin, smooth sleeve in the small dimensionings of the structural type indicated, particularly because this sleeve must be fixed in its working position by means of friction so that it can not loosen unintentionally and because, in addition, the outer casing of this sleeve serving as a hold is moistened by saliva during practical use and this makes manual handling difficult. This deficiency becomes especially clear when it is mentioned that the locking sleeve of such an angle piece has an outer diameter of 6 mm at most; that is, it is substantially thinner than a pencil.

It is the object of the present invention to avoid the disadvantages of the known angle pieces with respect to the bearing and replacement of the drilling tool, as well as the disadvantages of the locking apparatus, without restricting the possibilities of producing such an angle piece with a cylindrically smooth head shape, as well as in miniature constructional form. This is achieved, according to the invention, in that a head bearing on the tool side, which head bearing is insertable in the head part in a form-locking manner, is rotatably and undetachably connected with the tool and in that an outer screw sleeve, which is axially displaceable on the head shaft, partially overlaps the head bearing in its inserted position. The head bearing, which is combined with the tool shaft, is rotatably supported with its bearing borehole on a neck extension of the driven gear wheel, which is located behind it and is securely connected with the tool shaft, and the head bearing is held in position by means of a shoulder ring which is pressed on the tool side against the bearing cylinder of the gear wheel and overlaps this cylinder, and accordingly also the bearing borehole of the head bearing, in diameter. In order to fasten the bearing of the tool shaft in the assigned recess of the angle piece head axially as well as radially in the operating position, the screwable sleeve, which is rotatably supported on the head shaft, is provided, in a construction of the invention, with an inner cone at its opening facing the tool, which inner cone can be joined and screwed on against a corresponding outer cone section attached on the tool bearing, wherein the action of the cone surfaces presses the bearing member axially, as well as radially, in its retainer. In order to be able to apply the required screw forces without difficulty, it is suggested, according to the invention, to construct the end of the screwable sleeve, which end is reinforced in diameter and is adjacent to the handle part of the angle piece, as a longitudinally grooved turning handle which preferably forms the transition of the handle part to the substantially smaller cylindrical section of the angle head as a lengthened cone. In addition, it is suggested to construct the cylindrical part of the screwable sleeve, which cylindrical part acts on the tool bearing, and the angle piece, which projects out over the latter, so as to have the same outer diameter; this is shown with the aid of the drawings.

Figure 2:
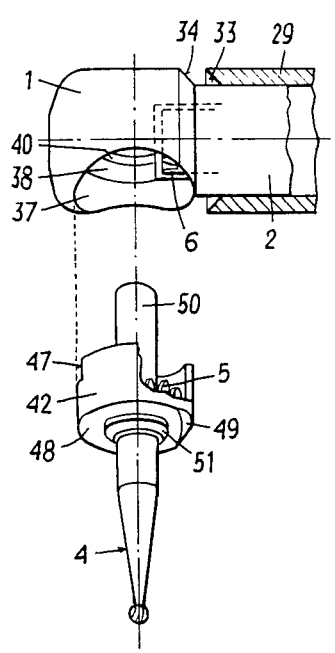
Figure 3:
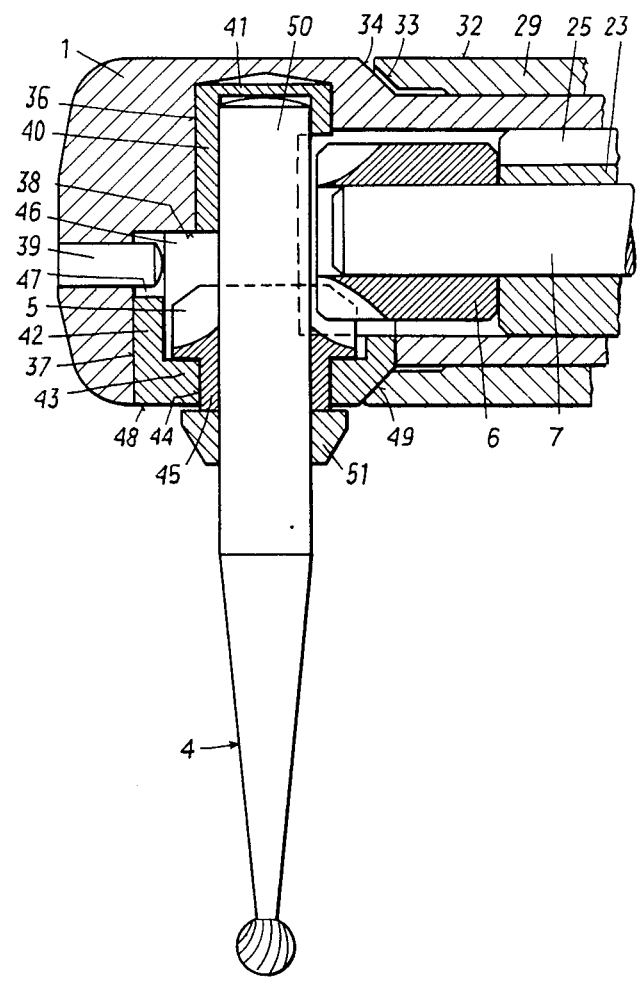
Figure 4:
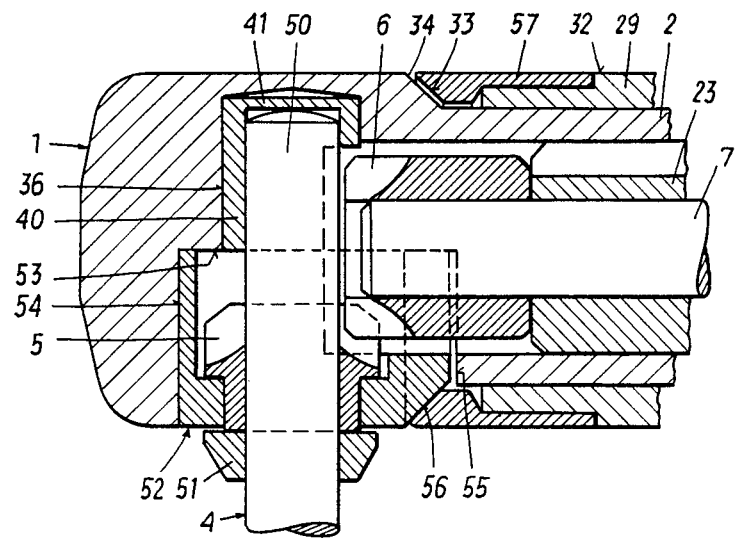
Figure 5:
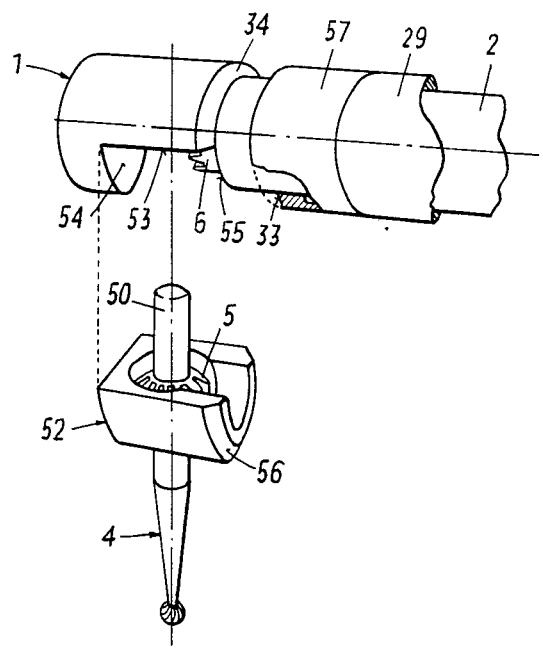

The invention is explained in more detail with the aid of the drawing showing;

FIG. 1 a longitudinal section through the angle piece until the angled transition to the handle part of same;

FIG. 2 a perspective view of an angle piece head, according to FIG. 1, with removed tool part;

FIG. 3 an angle piece head, according to FIG. 1, with inserted tool part and cylindrical front bearing, in section;

FIG. 4 an angle piece head as in FIG. 3, but with front bearing in the form of a semi-round head segment;

FIG. 5 an angle piece head, according to FIG. 4, with removed tool part, in perspective view.

The drilling tool 4 is rotatably supported in the head part 1 of an angle piece according to FIG. 1, which head 1 is connected with the handle part 3 via an elongated cylindrical shaft 2, and is driven by a pair of gear wheels 5, 6 which are driven in turn by the main axle 10 via a shaft 7 penetrating the head shaft and a pair of gear wheels 8, 9 arranged prior to the shaft 7. The handle part 3 and main axle 10 are connected in a generally known manner with motor drives, as a rule, by means of detachable plug couplers.

The connection between the head shaft 2 and the angled handle part 3 is produced by means of a threaded bush 11 which is screwed into the handle part 3 by means of a threaded projection 12 and receives the head shaft 2 and its bearing 15 on the handle side in a through-going graduated borehole 13, 14, the bearing 15 on the handle side being screwed with the head shaft via a thread 16 and overlapping the threaded neck 12 of the bush 11 with a flange 17. The flange 17 is clamped between the threaded neck 12 and the annular step 18 of the handle part 3, for which purpose a slight air gap 21 is provided between the adjacent end faces 19 and 20 of the parts 3 and 11 when screwing together the latter. Accordingly, when screwing together the parts 3 and 11 the head shaft 2 is fixed in its position relative to the angled handle part 3, wherein consists the possibility of selecting the position of the tool axis of the angle head 1 relative to the angular plane of the handle part 3 as desired prior to screwing together the parts 3, 11, since head shaft 2 and bearing member 15 are rotatably supported in the graduated borehole 13, 14 of the threaded bush 11 with a narrow sliding fit. The axial positioning of the shaft 7 results in that this shaft is reduced to a smaller diameter at its entrance into the rear bearing 15 and is supported against the bearing with the annular shoulder formed thereby and is held in this position by means of the drive wheel 8 mounted on the shaft extension 22. The bearing 23 on the head side is mounted on the shaft in the same manner, but is not securely connected with the head shaft 2, being, instead, displaceably supported in its borehole 24. Bearings 15 and 23 are provided with axial passages 25 serving to allow the passage of oil which is sprayed into the handle part of such angle hand pieces from spray bottles when subsequently lubricating these and all other bearings according to current practice.

With a tapered section 26, the threaded sleeve 11 forms the extension of the handle part 3 and ends on the head side in a threaded extension 27 which can be screwed into the female thread 28 of a rotationally movable sleeve 29 supported on the head shaft 2. This sleeve 29 forms the transition from the angle head 1 to the tapered shaping of the threaded bush 11, engages in an annular groove 30 of the threaded bush 11, passes, with a tapered section 31, into a cylindrical part 32 which has the same diameter as the head 1 and whose bore opening can be made to contact at the transition between head shaft 2 and head 1 with an inner core 33 against the likewise conical annular step 34. The sleeve 29 is provided with gripping grooves 35 on the cone casing 31, which gripping grooves enable the sleeve 29 to be turned by hand so as to screw and to be tightened against the head. The depth of the annular groove 30 is dimensioned in such a way that the sleeve 29 can be screwed away from the head 1 until the cone projection 34 of the head is released, as shown in FIG. 2.

A graduated borehole, which is formed from a blind hole 36 and a larger borehole 37, is arranged in the head 1 so as to be transverse relative to the drive axle, wherein the borehole 37 extends in the direction of the tool and passes into the borehole 36 in the center of the head above a plane surface 38. The two boreholes are connected with the drive borehole in order to permit the tooth engagement of the drive wheels 5, 6. A pin 39 is fastened in the head near the plane surface 38 transversely relative to the borehole 37 and opposite the gear wheel 6 and projects into the borehole 37. A slide bearing 40 is fastened in the blind borehole 36, the inner diameter of which slide bearing 40 is adapted to the shaft diameter of the drill and is closed at the base of the borehole by means of a wall 41 in order to axially support the drill shaft. A potlike bearing 42 of a cylindrical basic shape is detachably held in the borehole 37, strikes against the graduated surface 38 and closes with the outer diameter of the head 1. An inner collar 43 of this bearing forms the closure, on the tool side, of the angle piece head and the front bearing of the latter simultaneously in that its through-borehole 44 receives a cylinder neck 45 of the head drive 5 so as to allow rotational movement and also axially supports the drive 5. The hollow space 46 of the bearing member 42 is formed by means of cylindrical bores or recesses which are somewhat larger than the diameter of the gear wheels 5, 6 projecting into the bearing member. A slot 47 penetrates the sleevelike wall of the bearing 42 and is made to engage with the pin 39 in order to secure the bearing against turning and in order to be able to insert this bearing in the head in fundamentally only one and the same position, respectively. In order to hold the bearing 42 in position a tapered chamfer 49 is arranged on its end face 48, the casing surface or generated surface of which chamfer 49 corresponds with the hollow cone 33 of the sleeve 29 and projects slightly over the cone projection 34 of the head with reference to the drill axis in the direction of the sleeve 29 and the sleeve 29 can now be screwed against the chamfer 49. The force effect via the cones 33, 49 results in that the bearing is held in position axially as well as radially, in that the force-locking connection is well-secured against automatic loosening as a result of the cone action and in that the bearing can not be turned out of its position during tightening and loosening of the screw connection as a result of the support by means of the pin 39.

The drilling tool 4 is securely connected with the head drive 5, wherein the cylindrical shaft 50 of the tool projects over the drive at its end and is rotatably supported in the bearing 40 of the head in the operating position. In addition, the front bearing 42 is rotatably supported on the neck extension 45 of the drive wheel 5 by means of a ring 51 fastened on the tool shaft 50 in that the ring 51 overlaps the neck of the drive wheel and prevents the bearing from falling from the drive wheel. In this manner the tool shaft 50, drive wheel 5, front bearing 42 and ring 51 are connected to form a constructional unit which is inserted and exchanged in the head 1 only as a whole and whose locking is effected by means of the clamping action of the screw sleeve 29, as described above. It is particularly advantageous that the screw sleeve 29 be constructed so as to be reinforced at its end and provided with gripping grooves because the manipulation for tool replacement thereby moves from the actual angle head in the direction of the handle piece and can be carried out there with the necessary secure gripping more easily than was previously known.

The described construction unit of the drill tool 4 is shown in FIG. 2 in front of the opening of the angle head 1 and all described structural component parts can be seen there. In this illustration, the screw sleeve 29 is drawn in the position away from the head 1 and its cone face 34, which position sufficiently frees the head borehole 37 for the purpose of introducing the tool and its bearing 42.

The front bearing 42 need not necessarily have the cylindrical basic shape previously described. Particularly when the angle head has a particularly small dimensioning, as required for the treatment of children or as also seems desirable in other cases of parts of the human jaw which are extremely difficult to reach, and with respect to the fact that the bearing must always have a smaller outer diameter than the head diameter, it seems advisable to reinforce this bearing and to construct it so as to be more compact than the cylindrical basic shape allows. For this reason it is suggested, according to FIGS. 4 and 5, to employ a bearing member 52 whose external shape is a cut out section from the angle head 1. Accordingly, the bearing member is a semicircular cylinder segment lying transversely relative to the drill axis, which cylinder segment is insertable in an adequate recess with boundary surfaces 53, 54 and 55 of the head 1 and is to be fastened there by means of the clamping action of the screw sleeve 29. The fastening is effected, as described above, by means of the action of the inner cone 33 of the sleeve 29 against a tapered chamfer 56 of the bearing 52 and the pressing of the bearing is expected against the surfaces 53 and 54 of the head 1, wherein the bearing body is simultaneously centered relative to the axis of the head. The centering action is made possible in that the cone 56 is constructed over the full semicircle of the bearing member 52 and is therefore compulsorily drawn by the screw sleeve 29 into its axial position. The bearing member 52 projects out somewhat farther in the direction of the screw sleeve 29 than toward the other sides; it is thereby reinforced in the area of the cone face 56 and is asymmetrical with reference to the drill axis and can therefore only be inserted compulsorily in this position—but not so as to be incorrectly turned by 180°—in the head. It is also no longer necessary to fix the bearing member by means of a pin as described in FIG. 3. The tool, together with the bearing 52, is shown in FIG. 4 in the operating position within the head 1. The drive and the bearing of the tool, as well as its locking and replacement, are effected in a corresponding sense as shown in FIGS. 1-3.

In order to reduce the wear of the screw sleeve 29 at its hollow cone 33 the opening of the sleeve on the head side can be advantageously formed by means of a ring 57 arranged in front of it and composed of particularly resistent material, which ring 57 is connected with the screw sleeve 29 so as to be fixed or rotatable and it permits the screw sleeve itself to be produced, for example, from light metal or similar material for reasons of weight reduction.

The invention is not limited to the embodiment forms described and shown by way of example and it allows for additional constructions and modifications. Thus it is possible, for example, when the drive gear wheels are correspondingly dimensioned, to unite the bearing of the tool shaft placed in the head with the front bearing on the tool side, to integrate them accordingly in the constructional unit of the tool and to construct them so as to be likewise interchangeable. In addition, roller bearings can be employed in place of slide bearings; the bearing members can project forward over the head shaping or the angle head can be larger than the neck piece of the screw sleeve. It is also possible to attach seals at bearings or connection points or to arrage lines for supplying cooling media, e.g. within the angle head or at its outer surface. Finally, the drive of the tool need not be rotating, but can also be a rotating pendulum drive, such as is known for dental filing angle pieces and where various root canal files are used instead of drills.

I claim:

1. Angle piece for dental purposes comprising a head shaft, a head part, and a tool with cylindrical tool shaft, which tool is supported in the head part transversely relative to the drive axis of the head shaft, said tool securely connected with its drive gear wheel and interchangeable together with the latter, characterized in that a head bearing (42) is rotatably and axially immovably connected with said tool (4), wherein said head bearing is stationary when inserted in said head part, and in that an outer screw sleeve (29) which is axially displaceable on the head shaft (2) partly overlaps said head bearing (42) in its inserted position.

2. Angle piece according to claim 1, characterized in that the opening of said screw sleeve (29) has a hollow cone (33) which is pressable against a corresponding outer one face (49) of said head bearing (42), wherein said hollow cone (33) and said outer cone face (49) extend at the same angle relative to the tool axis.

3. Angle piece according to claim 2, characterized in that said head bearing (42) has a cylindrical outer shape and said outer cone face (49) is arranged at the transition of the end face (48) on the tool side to the cylindrical casing surface or generated surface (42).

4. Angle piece according to claim 1, characterized in that said head bearing (42) is secured against turning in the insertion position by means of a pin (39) arranged in said head part (1), which pin (39) engages in a slot (47) of said head bearing.

5. Angle piece according to claim 1 or 2, characterized in that the outer shape of said head bearing (52) is a segment of said head part (1) and said outer cone face (56) is arranged on the end face of said segment, which end face faces said screw sleeve (29).

6. Angle piece according to claim 1, characterized in that said screw sleeve (29) enlarges conically at its end which is remote of said head part (1) and is constructed as a turning handle (31).

7. Angle piece according to claim 1, characterized in that said head part (1) is connected with said head shaft (2) and said screw sleeve (29) is connected with a base part (11), wherein said base part (11) can be screwed into said handle part (3).

8. Angle piece according to claim 1, characterized in that the outer diameter of said head part (1) and the outer diameter of the section (32) of said screw sleeve (29) adjoining said head part are of equal size.

* * * * *

UNITED STATES PATENT AND TRADEMARK OFFICE
CERTIFICATE OF CORRECTION

PATENT NO. : 4,564,354
DATED : January 14, 1986
INVENTOR(S) : Otto Rosenstatter

It is certified that error appears in the above-identified patent and that said Letters Patent is hereby corrected as shown below:

In the heading of the Patent, it should read:

-- [73] Assignee: Dentalwerk Bürmoos Gesellschaft m.b.H.,

Bürmoos, Austria

Signed and Sealed this

Twenty-fourth Day of May, 1988

*Attest:*

DONALD J. QUIGG

*Attesting Officer*　　　*Commissioner of Patents and Trademarks*